(12) United States Patent
Bruin et al.

(10) Patent No.: US 10,441,732 B2
(45) Date of Patent: Oct. 15, 2019

(54) END FITTING FOR DISPOSABLE SPACER

(71) Applicant: CLEMENT CLARKE INTERNATIONAL LTD, Harlow, Essex (GB)

(72) Inventors: Ronald Bruin, Harlow (GB); Mark Sanders, Dunstable (GB)

(73) Assignee: Clement Clarke International Ltd., Essex (GB)

( * ) Notice: Subject to any disclaimer, the term of this patent is extended or adjusted under 35 U.S.C. 154(b) by 425 days.

(21) Appl. No.: 15/502,521

(22) PCT Filed: Aug. 11, 2015

(86) PCT No.: PCT/GB2015/052312
§ 371 (c)(1),
(2) Date: Feb. 8, 2017

(87) PCT Pub. No.: WO2016/024099
PCT Pub. Date: Feb. 18, 2016

(65) Prior Publication Data
US 2017/0232212 A1    Aug. 17, 2017

(30) Foreign Application Priority Data

Aug. 13, 2014 (GB) .................................. 1414349.9
Mar. 25, 2015 (GB) .................................. 1505048.7

(51) Int. Cl.
*A61M 15/00* (2006.01)
(52) U.S. Cl.
CPC ...... *A61M 15/0025* (2014.02); *A61M 15/002* (2014.02); *A61M 15/0086* (2013.01)
(58) Field of Classification Search
CPC .............. A61M 15/00; A61M 15/0086; A61M 15/0025; A61M 15/0026; A61M 15/0028;
(Continued)

(56) References Cited

U.S. PATENT DOCUMENTS 4,428,498 A    1/1984   Obey
4,953,545 A    9/1990   McCarty
(Continued)

FOREIGN PATENT DOCUMENTS

EP    1 358 901       11/2003
GB    2491178 A       11/2012

OTHER PUBLICATIONS

The International Search Report for PCT/GB2015/052312 dated Oct. 6, 2015, pp. 1-7.
(Continued)

Primary Examiner — Manuel A Mendez
(74) Attorney, Agent, or Firm — McDonnell Boehnen Hulbert & Berghoff LLP

(57)   ABSTRACT

The present invention provides an end fitting (1) for a spacer assembly and a spacer assembly having such an end fitting for fitting to a drug delivery inhaler device (21). The spacer assembly has a spacer body (17) with opposing first and second axial ends. The end fitting comprises an end panel having an upper end face (2) and a lower end face (3). A lower annular recess (4) is provided on the lower end face for receiving the first axial end (18) of the spacer body in a first configuration. An upper annular recess (12) is provided on the upper end face for receiving the second axial end (20) of the spacer body in a second configuration. The end fitting further comprises an open-ended tubular projection (16) extending from the upper end face and an aperture extending through the end panel from the lower end face to the tubular projection.

20 Claims, 4 Drawing Sheets

(58) Field of Classification Search
CPC .......... A61M 15/0066; A61M 15/0088; A61M 16/20; A61M 15/009; A61M 15/0045; A61M 15/0065; A61M 15/0091; A61M 15/08; A61M 11/06; A61M 15/002; B65D 83/54; B65D 83/38; B65D 83/48; A61J 1/2096; A61J 1/2089; A61K 9/0075
See application file for complete search history.

(56) References Cited

U.S. PATENT DOCUMENTS

| | | |
|---|---|---|
| 5,848,588 A | 12/1998 | Foley et al. |
| 2009/0013993 A1 | 1/2009 | Bird et al. |

OTHER PUBLICATIONS

The Written Opinion of the International Searching Authority for PCT/GB2015/052312 dated Oct. 6, 2015, pp. 1-7.
Willemse, B.W. et al. "Use of a paper disposable cup as a spacer is effective for the first-aid management of asthma" Respiratory Medicine (2003) vol. 97(1), pp. 86-89.

END FITTING FOR DISPOSABLE SPACER

CROSS-REFERENCE TO RELATED APPLICATION

This application is a national stage application of International Patent Application No. PCT/GB2015/052312 filed Aug. 11, 2015, which claims priority to United Kingdom Patent Application No. 1414349.9filed Aug. 13, 2014, and to United Kingdom Patent Application No. 1505048.7 filed Mar. 25, 2015, all are which hereby incorporated by reference in their entirety.

FIELD OF THE INVENTION

The present invention relates to a spacer assembly for fitting to a drug delivery inhaler devices, such as a pressurised metered dose inhaler (pMDI) devices or a dry powder inhaler (DPI) device. In particular, this invention relates to an end fitting for a disposable spacer assembly for fitting to a drug delivery inhaler device.

BACKGROUND TO THE INVENTION

Pressurised metered dose inhaler (pMDI) devices are the most popular and widely prescribed devices for respiratory drug delivery for treatment of asthma and other respiratory conditions.

In such devices, the active ingredient/drug is typically provided in the form of a solution or suspension held in a pressurised canister. Actuation of the canister is typically achieved by depressing the canister towards the body of the device. This causes an interaction between the canister and a valve seat that causes a metered dose to be ejected from the canister, along with a propellant gas (typically a hydrofluoroalkane (HFA) gas). The dose becomes aerosolized and available for inhalation by the patient.

Dry powder inhaler (DPI) devices are an alternative to these aerosol-based inhalers, and well known in the art, in which a powdered respiratory drug may be held, for example, within a capsule which is perforated by the device as the patient inhales. An insufficient inhalation rate will result in reduced dose delivery and incomplete de-aggregation of the powdered drug potentially leading to poor control of the respiratory problem.

The perception is that these devices are easy to use but this is far from the reality: seemingly simple steps such as coordination of actuation of the device with inhalation, and inhaling at the appropriate flow rate are often performed incorrectly.

It is known to provide a spacer or a holding chamber to assist patients, especially young and elderly patients, with their inhaler use. These adapters are known to improve the direction and deposition of medication delivered by drug delivery inhaler devices.

Spacers are relatively simple adapters (often in the form of a simple tube or chamber) which extend the mouthpiece of the drug delivery inhaler devices thus slowing and directing the medication into the patient's lungs rather than impacting and sticking to the back of their mouth.

Holding chambers are provided with a valve, typically a one-way valve allowing inhalation from but not exhalation into the chamber, and the medication is trapped within the holding chamber allowing the medication to be inhaled slowly. The use of these valved holding chambers eliminates the requirement that slow deep inhalation coincides with the actuation of the pMDI drug delivery inhaler device.

It is known to use non-conventional devices as spacers for use with drug delivery inhaler devices. For example, Sheth et al. (Annals of Allergy, Asthma and Immunology, 113 (2014) 55-62) discuss the successful use of various household items such as a toilet paper roll, a paper towel paper roll, rolled paper and a plastic bottle as spacers for use with a pMDI. Paper cups have also been proposed as an effective spacer (Wllemse, et al. Respiratory Medicine, 97 (2003), 86-89). In this study, the mouthpiece of the pMDI was inserted into a cross-cut formed in the base of the paper cup and the pMDI actuated whilst the opening of the cup was blocked with a user's hand. The user then removed their hand and inhaled from the cup opening.

These non-conventional spacers have the advantage that they are low cost and easily available without a prescription and yet they have proved to be clinically effective.

Whilst such spacers may be ideal for developing countries, they are not, however, suitable for some settings in which there is a requirement for low-cost, disposable spacers. For example, a recent UK Government initiative requires UK schools to provide drug delivery inhaler devices and spacers for emergency use within the school (http://www.asthma.org.uk/get-involved-inhalers-in-schools).

Known, conventional plastic spacers require thorough cleaning after use, especially if they are to be used by more than one patient and hence this cleaning places a burden on the school staff and a contamination risk if cleaning is not carried out effectively. The non-conventional devices discussed above, whilst cheap and disposable, are unlikely to meet the requirements for spacer provision set by the UK Government.

Inserting a pMDI mouthpiece into a cross-cut in the base of a paper cup as described above, will not form a good seal and so there may be leakage and wastage of the drug. Furthermore, this arrangement is incapable of directing the angle of entry of the drug plume into the cup body. Finally, any lose paper pieces or dust will interfere with the drug flow and could be inhaled by the user.

WO01/05458 describes a disposable, cardboard holding chamber which contains two one-way valves. The mouthpiece is provided by two holes in the cardboard. Such a mouthpiece will be unfamiliar to a child and they may also find it difficult to form a seal around these holes.

Accordingly, there is a need for a low cost, disposable spacer that can easily be used by children (as well as other patients).

SUMMARY OF THE INVENTION

Accordingly, in a first aspect, the present invention provides an end fitting for a spacer assembly for fitting to a drug delivery inhaler device, said spacer assembly having a spacer body with opposing first and second axial ends, the end fitting comprising:

an end panel having an upper end face and a lower end face;

a lower annular recess on the lower end face for receiving the first axial end of the spacer body in a first configuration;

an upper annular recess on the upper end face for receiving the second axial end of the spacer body in a second configuration;

an open-ended tubular projection extending from the upper end face; and an aperture extending through the end panel from the lower end face to the tubular projection.

According to a second aspect of the present invention, there is provided a spacer assembly for fitting to a drug delivery inhaler device, said spacer assembly comprising:

a spacer body having opposing first and second axial ends; and at least one end fitting according to the first aspect of the present invention; wherein the first axial end is received in the lower annular recess of the end fitting or wherein the second axial end is received in the upper annular recess of the end fitting.

According to a third aspect of the present invention, there is provided a spacer assembly kit for providing a spacer assembly for fitting to a drug delivery inhaler device, said kit comprising:

a spacer body having opposing first and second axial ends;

at least one end fitting according to the first aspect of the present invention.

The end fitting of the first aspect of the present invention is adapted so that it can be fitted to either of the opposing axial ends of a spacer body by using either the lower annular recess (in a first configuration) or upper annular recess (in a second configuration).

In the first configuration, the open-ended tubular projection on the upper end face forms a mouthpiece and the aperture on the lower end face is for providing fluid communication from within the spacer body to the mouthpiece. The projecting mouthpiece will be familiar to a child and the child will be able to form a seal and use the spacer assembly with ease.

In the second configuration, the aperture is for receiving the mouthpiece of a drug delivery inhaler device and allowing fluid communication through the aperture and the open-ended tubular projection into the spacer body. In this configuration, the tubular projection can form a tight seal with the mouthpiece thus ensuring that it is held firmly in the correct orientation and there is no leakage/wastage of drug. In other words, unlike the known non-conventional devices (e.g. the paper cup), the end fitting ensures a standardization of the presentation of the pMDI device with respect to the spacer body (and therefore reproducible actuation of the drug into the spacer body and, thereafter, to the user).

Optional features of the invention will now be set out. These are applicable singly or in any combination with any aspect of the invention.

In preferred embodiments of the second aspect, the spacer assembly comprises a first end fitting according to the first aspect of the present invention and a second end fitting according to the first aspect of the present invention. The first axial end is received in the lower annular recess of the first end fitting and wherein the second axial end is received in the upper annular recess of the second end fitting.

In preferred embodiments of the third aspect, the kit comprises a first end fitting according to the first aspect of the present invention and a second end fitting according to the first aspect of the present invention.

Accordingly, when two such end fittings are provided (e.g. in a kit), one can be fitted to spacer body in its first configuration and one can be fitted to the spacer body in its second configuration to form the complete spacer assembly according to an embodiment of the second aspect.

Preferably, the/each end fitting is formed of a one-piece plastics material construction which enables it to be manufactured relatively inexpensively thus allowing it to be disposable. In some embodiments, the/each end fitting is formed of thermoplastics plastics material such polystyrene, acrylonitrile butadiene styrene, polyester copolymer, polyethylene terephthalate, polyethylene terephthalate glycol-modified, polycarbonate, polypropylene, polyethylene (sheet and foamed sheet), polyvinyl chloride, and polymethyl methacrylate. The end fitting may be formed by a vacuum forming process or other low-cost forming process. Materials are preferentially of food-grade.

In other embodiments, the/each end fitting may comprise at least one cellulosic material (e.g. derived from wood, rags or grasses) such as paper, paperboard, or cardboard. The/each end fitting may comprise a composite material including cellulosic material e.g. papier mâché or a plastics/paper composite.

The paper, paperboard and/or cardboard may be recycled paper, paperboard and/or cardboard.

In some embodiments of the second and third aspects, the spacer body is a disposable spacer body. For example, it could be formed of paper, paperboard, cardboard, plastics material, e.g. foamed plastics material (such as foamed polystyrene) or plastic/paper composite.

Where both the end fitting(s) and spacer body are formed of cellulosic material such as paper, paperboard, cardboard or a composite material containing such cellulosic material, the entire spacer assembly can be easily disposable/recyclable.

The spacer body may have a circular, oval or curvilinear cross-sectional profile. The spacer body may be tubular e.g. cylindrical but is preferably frusto-conical i.e. with one axial end having a greater cross-sectional profile/greater radius than the other. In preferred embodiments, the first axial end of the spacer body (i.e. the end for fitment into the lower annular recess in the first configuration) has a greater cross-sectional area/greater radius than the second axial end of the spacer body (i.e. the end for fitment into the upper annular recess in the second configuration).

In some embodiments, the spacer body could be provided by a disposable cup e.g. a paper cup (which may have a plastic or wax layer), polystyrene cup or other cup of materials known in the art, with the user removing the base of the disposable cup prior to use. Disposable cups are cheap, readily available and easily stored in stacks.

The lower annular recess may be defined at its radially outer limit by an annular flange extending downwardly from the end panel. In preferred embodiments, the annular flange may extend from around the periphery of the end panel.

The flange may include a skirt portion for facilitating centring of the end fitting as it is fitted in the first configuration with the first axial end of the spacer body in the lower annular recess. The skirt portion may extend substantially perpendicularly to the end panel or it may be flared away from the perpendicular.

The flange may have a curved gripping portion proximal the end panel (between the end panel and the skirt portion) such that the lower annular recess has a circumferential curvature at its radially outermost edge. This curved gripping portion is ideal for engaging the rim of the spacer body e.g. a beaded rim of a disposable cup/spacer body in a snap-fit engagement.

The lower annular recess may be defined at its radially inner limit by an outer face of a circumferentially-extending wall. The base of the outer face of the circumferentially-extending wall may be spaced from the aperture by a lower annular rim.

The upper annular recess may be defined at its radially outer limit by an inner face of the circumferentially-extending wall. The top of the circumferentially-extending wall may be spaced from the periphery of the upper end face by an upper annular rim. The top of the circumferentially-extending wall is preferably flush with the upper annular rim.

This arrangement of the upper and lower annular recesses with the circumferentially-extending wall and upper/lowers rims allows two or more end fittings to be stacked one upon another. During stacking, the lower annular rim of the uppermost end fitting projects into the upper annular recess of the adjacent lowermost end fitting and upper annular rim of the lowermost end fitting projects into the lower annular recess of the adjacent uppermost fitting.

Stackable end fittings minimise the necessary storage and shipping space needed.

The inner face of the circumferentially-extending wall is for engaging the second axial end of the spacer e.g. by a press-fit/interference fitting. In some embodiments, the base of the inner face of the circumferentially-extending wall is provided with an optional annular bead for engaging the second axial end of the spacer body e.g. the base of a disposable cup or the rim of a spacer body. In some embodiments, the base of the inner face of the circumferentially-extending wall meets the lower annular rim at an angle of between 5 and 10 degrees to the perpendicular, preferably at an angle of around 7 degrees. This facilitates stacking of the end fittings.

The upper annular recess may be defined at its radially inner limit by the tubular projection which may project from the axial centre of the upper end face.

Where the spacer body is frusto-conical with the first axial end having a larger cross-sectional area that the second axial end, e.g. where the spacer body is a disposable cup, the upper annular recess has a smaller circumference than the lower annular recess.

The open-ended tubular projection and/or aperture may have any cross-sectional profile e.g. a circular, oval, elongated oval or mandorla-shaped cross-sectional profile. In preferred embodiments, the cross-sectional profile may be a truncated oval (barrel-shaped) i.e. matching the cross-sectional shape of the mouthpiece of commonly-prescribed drug delivery inhaler devices.

In the first configuration, a tubular projection having a barrel-shaped cross-sectional profile provides a mouthpiece that is familiar in shape and function for the user and thus increases ease of use.

In the second configuration, a tubular projection and aperture having a barrel-shaped cross-sectional profile allows easy fitting (e.g. by a press-fit or interference fitting) of the mouthpiece of a drug delivery inhaler device into the aperture/tubular projection.

In preferred embodiments, the tubular projection is provided on the axial centre of the upper end face (e.g. projecting from the annular recess) and the aperture is provided on the axial centre of the lower end face (e.g. on the lower annular rim).

In some embodiments, the end fitting may be provided with a valve.

The valve may be any known one-way valve which allows inhalation from the spacer body but does not allow exhalation into the spacer body. In some embodiments, the valve comprises a slit silicone disc seated on a valve seat, the valve seat positioned across the aperture and allowing the disc to flex and the slits to open towards the opening of the tubular projection but preventing flexing of the disc and opening of the slots away from the opening of the tubular projection. In some embodiments, with a valve provided for use in the second configuration, the valve will be displaced into the open position by the insertion of the mouthpiece of the drug deliver inhaler device. In embodiments with valves provided for use in both configurations, the valves may be matching or different.

BRIEF DESCRIPTION OF THE FIGURES

Embodiments of the invention will now be described by way of example with reference to the accompanying drawings in which.

DETAILED DESCRIPTION OF PREFERRED EMBODIMENTS

Figure 1:
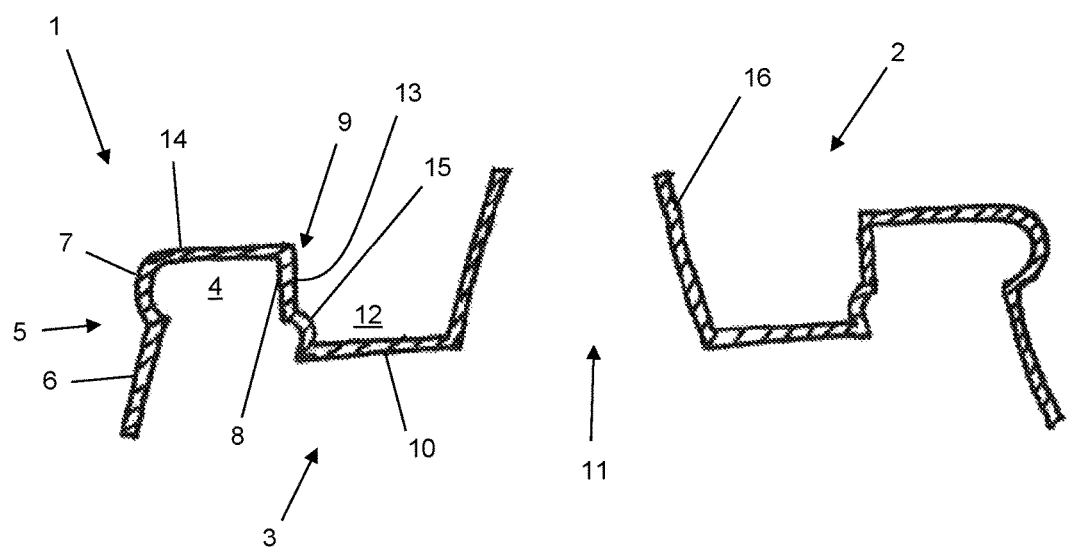
FIG. 1 shows a cross-sectional view of a first embodiment of an end fitting according to the first aspect of the present invention.

FIG. 1 shows a cross-sectional view of an end fitting according to the first aspect of the present invention. The end fitting comprises a circular end panel 1 having an upper end face 2 and a lower end face 3.

The lower end face 3 comprises a lower annular recess 4 which is defined at its radially outer limit by an annular flange 5 extending downwardly around the periphery of the end panel 1. The flange includes a flared skirt portion 6 and a curved gripping portion 7 proximal the end panel 1 such that the lower annular recess 4 has a circumferential curvature at its radially outermost edge.

The lower annular recess 4 is defined at its radially inner limit by an outer face 8 of a circumferentially-extending wall 9. The base of the outer face 8 of the circumferentially-extending wall 9 extends to a lower annular rim 10 having an aperture 11 at its axial centre.

The upper end face 2 includes an upper annular recess 12 which is defined at its radially outer limit by an inner face 13 of the circumferentially-extending wall 9. The top of the circumferentially-extending wall 9 is spaced from the periphery of the upper end face 2 by an upper annular rim 14. The top of the circumferentially-extending wall 9 is flush with the upper annular rim 14.

The base of the inner face 13 of the circumferentially-extending wall 9 is provided with an annular bead 15. The base of the inner face 13 of the circumferentially-extending wall and the lower annular rim 10 meet at an angle of seven degrees to the perpendicular.

The upper annular recess 12 is defined at its radially inner limit by the wall of an open-ended tubular projection 16 which projects from the axial centre of the upper end face 2.

The aperture 11 in the lower end face 3 opens to the tubular projection 16.

Figure 4:
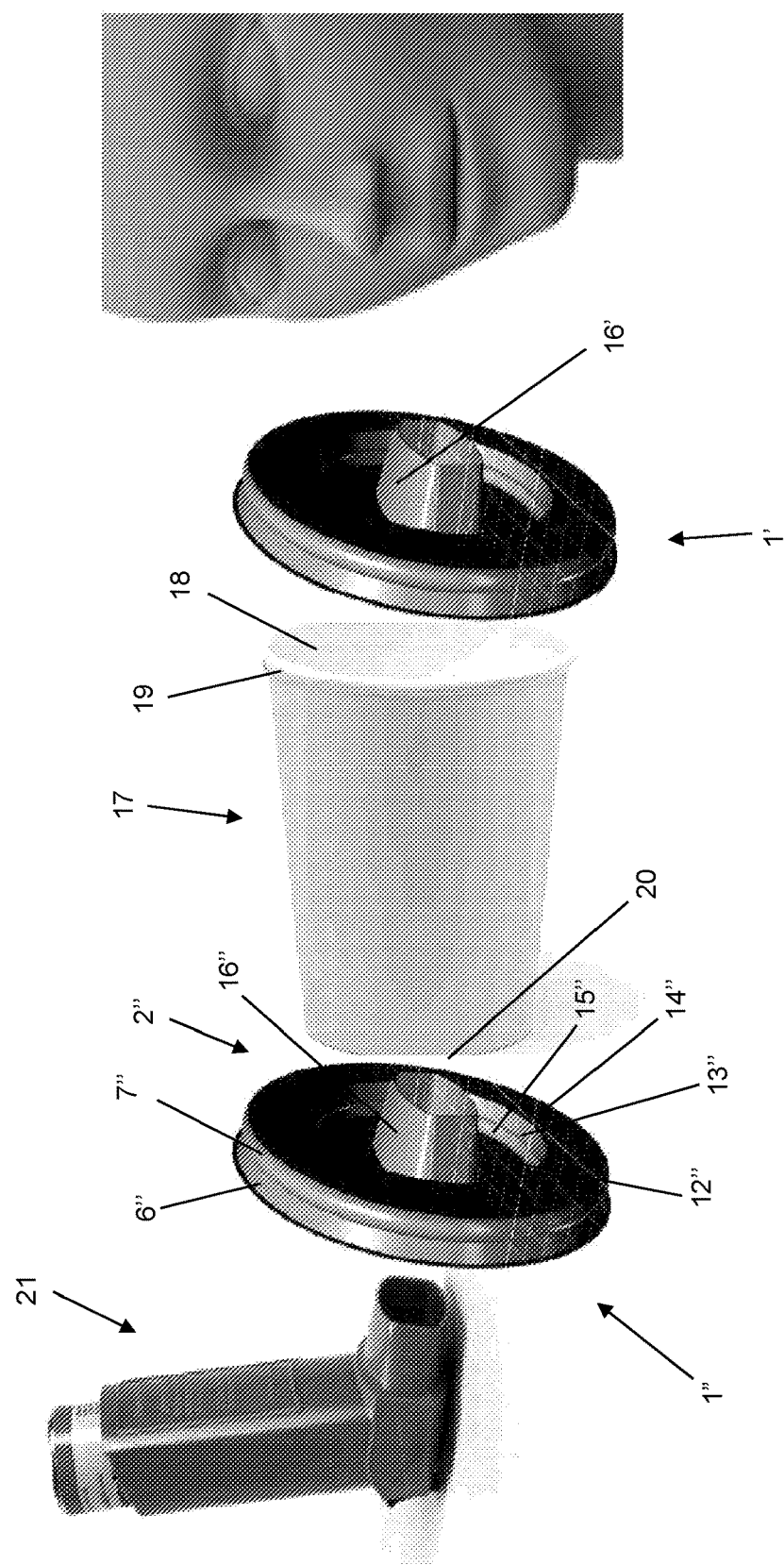
FIG. 4 shows an exploded view of a spacer assembly according to the second aspect of the present invention.

The open-ended tubular projection 16 and aperture 11 both have a truncated oval (barrel-shaped) cross-sectional profile as can be seen in FIG. 4.

The end fitting is formed of a one-piece construction by vacuum forming or other low-cost forming process of polystyrene or glycol-modified polyethylene terephthalate which enables it to be manufactured relatively inexpensively thus allowing it to be disposable. In other embodiments, the end fitting may be formed of a cellulosic material e.g. paper, paperboard or cardboard.

The end fitting will normally be provided in a kit with a number of identical end fittings. The end fittings are stackable one upon another with the tubular projection 16 of one end fitting being fitted into the aperture 11 of the adjacent end fitting and the upper/lower annular rims 14, 10 fitting into the lower/upper annular recesses 4, 12 of the adjacent end fitting. This minimises the necessary storage and shipping space needed.

Figure 2:
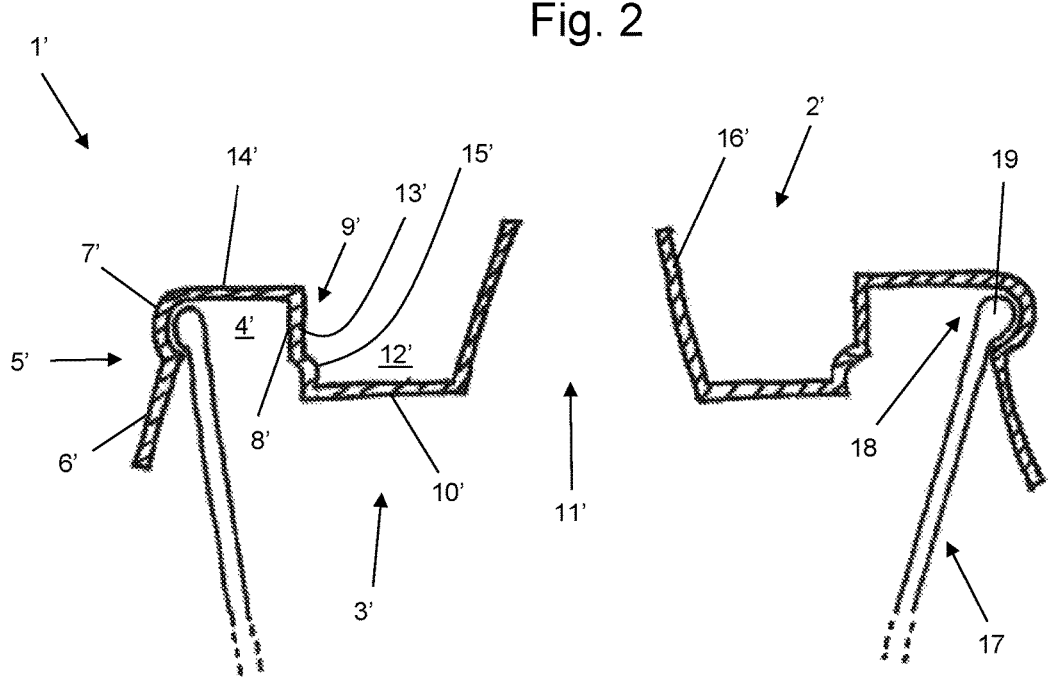
FIG. 2 shows a cross-sectional view the first embodiment in the first configuration.
Figure 3:
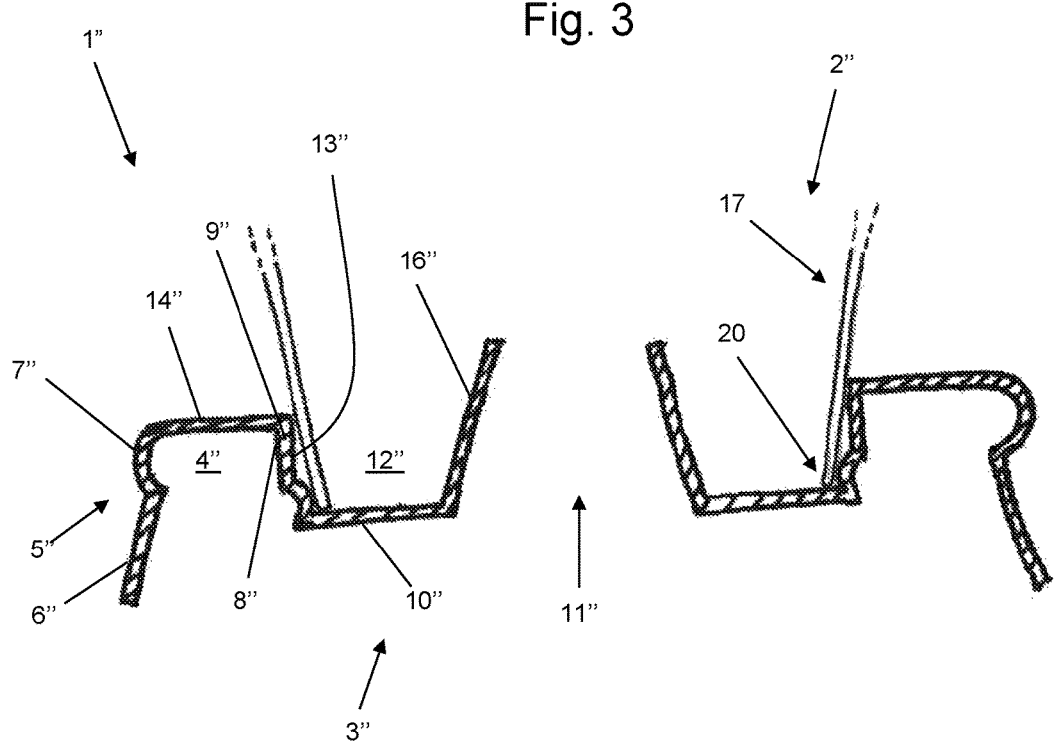
FIG. 3 shows a cross-sectional view of the first embodiment in the second configuration.

The end fittings are for use with a spacer body as shown in FIGS. 2 to 4.

In this embodiment, the spacer body is a disposable cup 17 which may be formed of paper (which may have a plastic or wax layer), polystyrene or similar materials. Disposable cups are cheap, readily available and easily stored in stacks.

The disposable cup has a first axial end 18 with a beaded rim 19 and a second axial end 20 at its base. The user will remove the base of the disposable cup 17 prior to use as a spacer body.

The first axial end 18 has a greater circumference than the second axial end 20

A first end fitting 1' is fitted in its first configuration to the beaded rim 19 of the first axial end 18 of the disposable cup 17 as shown in FIG. 2.

The skirt portion 6' of the flange 5' is used to facilitate centring of the first axial end 18 of the disposable cup 17 as the first end fitting is pushed down into engagement with the first axial end 18. The beaded rim 19 is received in the annular recess 4' and gripped by the curved gripping portion 7'. The flange 5' is resiliently flexible such that a snap-fit connection is formed between the first axial end 18/beaded rim 19 and the curved gripping portion 7'.

A second end fitting 1" is fitted in its second configuration to the second axial end 20 of the disposable cup 17 as shown in FIG. 3.

The second axial end 20 of the disposable cup is pressed into the upper annular recess 12" in abutment with the outer face 13" of the circumferentially-extending wall 9". The base of the inner face 13" of the circumferentially extending wall 9" and the lower annular rim 10" grip the second axial end and retains it within the upper annular recess 12" in a press-fit/interference engagement.

Thus it can be seen that the end fitting described above can be fitted to either of the opposing axial ends 18, 20 of the disposable cup 17 by using either the lower annular recess 12 (in the first configuration) or upper annular recess 4 (in the second configuration).

As shown in FIG. 4, a spacer assembly comprises both a first end fitting 1' in its first configuration and a second end fitting 1" in its second configuration.

In the first configuration at the first axial end 18, the open-ended tubular projection 16' on the upper end face 2' forms a mouthpiece and the aperture 11' on the lower end face 3' is for providing fluid communication from within the disposable cup 17 to the mouthpiece. The projecting mouthpiece will be familiar to a child and the child will be able to form a seal and use the spacer assembly with ease.

In the second configuration at the second axial end, the aperture 11" is for receiving the mouthpiece of a drug delivery inhaler device 21 and allowing fluid communication through the aperture 11" and the open-ended tubular projection 16" into the disposable cup 17.

In use, the patient or carer first affixes the first end fitting 1' to the first axial end 18 and the second end fitting 1" to the second axial end 20.

The mouthpiece of a pMDI 21 is inserted into the aperture 11" of the second end fitting 1" to form a press-fit/interference engagement.

Next, the use inserts the tubular projection 16' on the first end fitting 1' into their mouth and actuates the pMDI 21 by depressing the canister.

The aerosolized drug particles pass from the pMDI 21 mouthpiece through the aperture 11" of the second end fitting 1" and into the disposable cup 17. The user then inhales through the tubular projection 16' of the first end fitting 1' to inhale the aerosolized drug particles.

After use, the end fittings 1', 1" can be discarded into refuse or recycling as can the disposable cup 17.

EXAMPLES

A number of examples were carried out using an inventive spacer assembly having a first end fitting in its first configuration and a second end fitting in its second configuration as shown in FIG. 4.

Example 1—Preliminary In Vitro Research

Preliminary in vitro research with the inventive spacer assembly was carried out comparing salbutamol sulphate delivery from Ventolin® HFA pMDI (GSK, 90 μg ex-mouthpiece 108 μg ex-valve) alone (n=5) and in combination with the inventive spacer assembly (n=3).

Devices were attached to an 8-stage Andersen Cascade Impactor, with drug, Impactor and devices used according to manufacturers' instructions and regulatory methodology (28 L/min flow rate, and representative of adult use). In addition to the standard actuation procedure, data were also collected when a one second delay was introduced between actuation and Impactor function to mimic sub-optimal use conditions.

Particle size and dose fractions (% valve label) were determined. Fine particle dose data±standard deviation (SD) are given in Table I.

TABLE 1

| Devices | mean Fine particle dose particle size <5 μm (mean μg ± SD) | |
| --- | --- | --- |
|  | Optimal use | Sub-optimal use |
| pMDI alone (n = 5) | 55.1 ± 4.55 | 10.2 ± 2.17 |
| pMDI + inventive spacer assembly (n = 3) | 56.6 ± 5.65 | 37.7 ± 7.65 |

The mean fine particle dose from the pMDI alone and from pMDI plus the inventive spacer assembly were very similar. When used sub-optimally—a situation easily envisaged in non-routine and emergency situations—the pMDI plus the inventive spacer assembly performed much better than the pMDI alone, delivering 37.7 μg. Since it is considered that delivering a lung dose of approximately 20 μg is the minimum necessary for a clinical effect, these are reassuring data.

Example 2—Intra-sample and Inter-sample Aerosol Performance of the Inventive Spacer Assembly In vitro research, conducted to US Food & Drug Administration (FDA) requirement standards, was carried out comparing the aerosol characteristics of salbutamol sulphate delivery from Ventolin® HFA pMDI (GSK) and from ProAir® HFA pMDI (Teva), both 90 μg ex-mouthpiece 108 μg ex-valve, via the inventive spacer assembly.

The pMDI plus inventive spacer assembly combinations were attached to an 8-stage Andersen Cascade Impactor (ACI), with drug, Impactor and devices used according to manufacturers' instructions (firing timing, cleaning routine, flow rate (28 L/min), analytical chemistry, data analysis etc.). Three samples of the inventive spacer assembly were tested on three occasions with each pMDI (18 tests in total). Total delivered dose, mass median aerodynamic diameter (MMAD), geometric standard deviation (GSD), and the various dose fractions (% valve label) were determined and analysed using analysis of variance (F-statistic value of less than 4.74 indicated no significant difference between samples at the 95% confidence level).

Representative mean±SD data are given in Table 2. There were no significant differences between the samples for all aerosol characteristics. The data were also typical for the pMDI device(s).

TABLE 2

| Aerosol characteristic (µg/actuation) | HFA pMDI + inventive spacer assembly (3 replicates) | | | |
|---|---|---|---|---|
| | Ventolin pMDI | F-statistic | ProAir pMDI | F-statistic |
| Total dose delivered | 49.03 ± 4.88 | 0.55 | 47.98 ± 5.13 | 0.60 |
| Total respirable dose (0.5-5.0 µm) | 40.70 ± 4.63 | 0.35 | 37.99 ± 4.64 | 0.41 |
| Fine particle dose (<4.7 µm) | 41.62 ± 4.31 | 0.27 | 38.96 ± 4.76 | 0.41 |

Example 3—Comparison of Aerosol Performance of the Inventive Spacer Assembly and OptiChamber® Diamond To the same standards and procedures as Example 2, the aerosol characteristics of salbutamol sulphate from Ventolin® HFA pMDI (GSK) and from ProAir® HFA pMDI (Teva) delivered via the OptiChamber® Diamond (OD, Philips Respironics) valved holding chamber (n=3) have been compared with the data from Example 2, and with pMDI alone (n=3).

One test per pMDI was carried out (12 tests in total). Data were analysed using Student's t-test with a two-tailed comparison between the inventive spacer assembly and OD. A t-value of less than 2.23 indicated no significant difference at the 95% confidence level.

The results are shown in Table 3 (inventive spacer assembly='new').

TABLE 3

| Aerosol characteristic (µg/actuation) | Ventolin pMDI | | | ProAir pMDI | | |
|---|---|---|---|---|---|---|
| | new | OD | pMDI | new | OD | pMDI |
| Total dose delivered | 49.0 ± 4.9 | 44.8 ± 3.4 | 103.8 ± 0.9 | 48.0 ± 5.1 | 43.2 ± 4.5 | 99.6 ± 4.6 |
| Total respirable dose (0.5-5.0 µm) | 40.7 ± 4.6 | 36.9 ± 3.2 | 42.2 ± 4.1 | 38.0 ± 4.6 | 35.4 ± 4.5 | 40.5 ± 4.2 |
| Fine particle dose (<4.7 µm) | 41.6 ± 4.3 | 38.8 ± 3.0 | 48.0 ± 2.7 | 39.0 ± 4.8 | 37.5 ± 4.5 | 46.2 ± 3.7 |

There were no significant differences between the above Ventolin and ProAir data for the inventive spacer assembly and OptiChamber Diamond (t statistic values, range 0.46-1.44). Total dose delivered data for pMDI alone demonstrate the contribution of the coarse particle fraction, <4.7 µm.

Example 4—Comparison of Aerosol Performance of the Inventive Spacer Assembly and Nessi® Spacer To the same standards and procedures as Example 2, the aerosol characteristics of salbutamol sulphate from Ventolin® HFA pMDI (GSK) delivered via the Nessi® (Hi-Tech Pharmacal Co.) spacer (n=3) have been compared with the data from Examples 2 and 3, and with pMDI alone (n=3). The Nessi® spacer is a rigid plastic valve-less spacer.

The results are shown in Table 4 (inventive spacer assembly='new').

TABLE 4

| Aerosol characteristic (µg/actuation) | Ventolin pMDI | | | |
|---|---|---|---|---|
| | new | OD | pMDI | Nessi |
| Total dose delivered | 49.0 ± 4.9 | 44.8 ± 3.4 | 103.8 ± 0.9 | 46.8 ± 0.6 |
| Total respirable dose (0.5-5.0 µm) | 40.7 ± 4.6 | 36.9 ± 3.2 | 42.2 ± 4.1 | 36.7 ± 0.6 |
| Fine particle dose (<4.7 µm) | 41.6 ± 4.3 | 38.8 ± 3.0 | 48.0 ± 2.7 | 38.2 ± 0.3 |

The Nessi® spacer data was comparable to the data for the inventive spacer.

Example 5—Comparison of Aerosol Performance of the Inventive Spacer Assembly, OptiChamber® Diamond and Nessi® Spacer at ACI Flow 12 L/Min Comparisons were repeated at a 12 L/min flow rate which is considered to be representative of paediatric and emergency use situations. Data were analysed using Student's t-test with two-tailed comparisons between the inventive spacer assembly and the other devices. A t-value of less than 2.78 indicated no significant difference at the 95% confidence level.

Spacer device comparisons at ACI flow 12 L/min showed no significant differences (t-value range 1.15-1.63) between the valve-less spacers: the new inventive spacer assembly and the Nessi® spacer (NS). The inventive spacer assembly was significantly different (t-value range 3.50-4.79) compared with the valved Optichamber® Diamond (OD) for all three variables, with the performance of the inventive spacer being superior.

The results are shown in Table 5 (inventive spacer assembly='new').

TABLE 5

| Ventolin pMDI | Aerosol characteristic (μg/actuation) | | |
|---|---|---|---|
| | Total dose delivered | Total respirable dose (0.5-5.0 μm) | Fine particle dose (<4.7 μm) |
| new | 55.6 ± 5.3 | 44.0 ± 5.1 | 43.9 ± 5.3 |
| OD | 36.9 ± 4.2 | 29.3 ± 4.9 | 29.8 ± 4.5 |
| NS | 49.2 ± 4.4 | 39.6 ± 3.8 | 39.7 ± 3.3 |
| | DS v OD | DS v NS | DS v OD | DS v NS | DS v OD | DS v NS |
| Difference | 18.7 | 6.44 | 14.7 | 4.4 | 14.1 | 4.1 |
| t-value | 4.79 | 1.63 | 3.64 | 1.21 | 3.50 | 1.15 |

Example 6—Comparison of Aerosol Performance of the Inventive Spacer Assembly, and the Lite-Aire® Spacer at ACI Flow 12 L/Min To the same standards and procedures as Example 5 and with a t-value of less than 2.78 indicating no significant difference at the 95% confidence level, the aerosol characteristics of salbutamol sulphate from Ventolin® HFA pMDI (GSK) delivered via the Lite-Aire® (Thayer Medical Corp) disposable valved holding chamber (n=3) and via the inventive spacer have been compared. The Lite-Aire® VHC is as described in WO01/05458 discussed above.

The results are shown in Table 6.

TABLE 6

| | Ventolin pMDI | | | |
|---|---|---|---|---|
| Aerosol characteristic (μg/actuation) | Inventive spacer | Lite-Aire | Mean Difference | t-value |
| Total dose delivered | 55.6 ± 5.3 | 30.6 ± 2.4 | 25.0 | 7.48 |
| Total respirable dose (0.5-5.0 μm) | 44.0 ± 5.1 | 21.0 ± 0.1 | 23.0 | 7.84 |
| Fine particle dose (<4.7 μm) | 43.9 ± 5.3 | 23.1 ± 0.6 | 20.8 | 6.73 |

Comparison between the valve-less inventive spacer and the (disposable) VHC Lite-Aire at ACI flow 12 L/min showed significant differences (t-values>6.73) between the two spacers. The inventive spacer delivered significantly higher respirable and fine particle particle doses.

While the invention has been described in conjunction with exemplary embodiments described above, many equivalent modifications and variations will be apparent to those skilled in the art. Accordingly, the exemplary embodiments of the invention set forth above are considered to be illustrative and non-limiting.

The invention claimed is:

1. An end fitting for a spacer assembly for fitting to a drug delivery inhaler device, said spacer assembly having a spacer body with opposing first and second axial ends, the end fitting comprising:
    an end panel having opposing first and second end faces;
    a first annular recess on the first end face for receiving the first axial end of the spacer body in a first configuration;
    second annular recess on the second end face for receiving the second axial end of the spacer body in a second configuration;
    an open-ended tubular projection extending from the second end face, the tubular projection forming a mouthpiece in the first configuration; and
    an aperture extending through the end panel from the first end face to the tubular projection to provide fluid communication from within the spacer body to the mouthpiece in the first configuration and for receiving the mouthpiece of a drug delivery inhaler device and allowing fluid communication through the tubular projection into the spacer body in the second configuration.

2. An end fitting according to claim 1 wherein the first annular recess is defined at its radially outer limit by an annular flange extending away from the first end face around the periphery of the end panel, the flange including a skirt portion and a curved gripping portion proximal the end panel for gripping the first axial end in the first configuration.

3. An end fitting according to claim 1 wherein the second annular recess is defined at its radially outer limit by an inner face of a circumferentially-extending wall, the circumferentially-extending wall being spaced from the periphery of the second end face by a second annular rim.

4. An end fitting according to claim 3 wherein the base of the inner face of the circumferentially-extending wall has an annular bead for engaging the second axial end of the spacer body in the second configuration.

5. An end fitting according to claim 3 wherein the first annular recess is defined at its radially inner limit by an outer face of the circumferentially-extending wall, the circumferentially-extending wall being spaced from the aperture by a first annular rim.

6. An end fitting according to claim 1 wherein the second annular recess is defined at its radially inner limit by the tubular projection.

7. An end fitting according to claim 1 wherein the open-ended tubular projection extends from the axial centre of the second end face.

8. An end fitting according to claim 7 wherein the aperture extends through the axial centre of the end panel.

9. An end fitting according to claim 1 formed of a one-piece plastics material construction.

10. An end fitting according to claim 1 comprising a cellulosic material.

11. An end fitting according to claim 1 further comprising a one-way valve, the valve comprising a slit silicone disc seated on a valve seat, the valve seat positioned across the aperture and allowing the disc to flex and the slits to open towards the opening of the tubular projection but preventing flexing of the disc and opening of the slots away from the opening of the tubular projection.

12. A spacer assembly for fitting to a drug delivery inhaler device, said spacer assembly comprising:
    a spacer body having opposing first and second axial ends; and
    at least one end fitting according to claim 1, wherein the first axial end is received in the first annular recess of the end fitting or wherein the second axial end is received in the second annular recess of the end fitting.

13. A spacer assembly according to claim 12 wherein the at least one end fitting comprises a first end fitting and a second end fitting, wherein the first axial end is received in the first annular recess of the first end fitting or wherein the second axial end is received in the second annular recess of the second end fitting.

14. A spacer assembly according to claim 12 wherein the spacer body and/or the at least one end fitting is formed of paper, paperboard, cardboard, plastics material or plastic/paper composite.

15. A spacer assembly according to claim 14 wherein the spacer body is a disposable cup.

16. A spacer assembly kit for providing a spacer assembly for fitting to a drug delivery inhaler device, said kit comprising:

a spacer body having opposing first and second axial ends; and at least one end fitting according to claims 1.

17. A spacer assembly kit according to claim 16 wherein the at least one end fitting comprises a first end fitting and a second end fitting.

18. A spacer assembly kit according to claim 17 wherein the first and second end fittings are stackable one upon the other.

19. A spacer assembly kit according to claims 16 wherein the spacer body and/or the at least one end fitting is formed of paper, paperboard, cardboard, plastics material or plastic/paper composite.

20. A spacer assembly kit according to claim 19 wherein the spacer body is a disposable cup.

* * * * *